(12) United States Patent
De Lacharrière et al.

(10) Patent No.: US 8,100,830 B2
(45) Date of Patent: Jan. 24, 2012

(54) NON-THERAPEUTIC METHODS OF EVALUATING SKIN NEUROSENSITIVITY, KIT AND USE OF A KIT FOR IMPLEMENTING THE METHOD

(75) Inventors: Olivier De Lacharrière, Paris (FR); Gilles Rubinstenn, Paris (FR); Roland Jourdain, Meudon la Forêt (FR)

(73) Assignee: Societe l'Oreal S.A., Paris (FR)

( * ) Notice: Subject to any disclaimer, the term of this patent is extended or adjusted under 35 U.S.C. 154(b) by 954 days.

(21) Appl. No.: 10/602,823

(22) Filed: Jun. 25, 2003

(65) Prior Publication Data

US 2004/0037776 A1  Feb. 26, 2004

Related U.S. Application Data

(60) Provisional application No. 60/395,349, filed on Jul. 12, 2002, provisional application No. 60/395,353, filed on Jul. 12, 2002.

(30) Foreign Application Priority Data

Jun. 25, 2002 (FR) ..................... 02 07869
Jun. 25, 2002 (FR) ..................... 02 07895

(51) Int. Cl.
*A61B 5/00* (2006.01)
(52) U.S. Cl. .......... 600/306; 600/557; 600/556; 424/9.8
(58) Field of Classification Search .................. None
See application file for complete search history.

(56) References Cited

U.S. PATENT DOCUMENTS 5,258,374 A   11/1993 Bianco
6,139,850 A * 10/2000 Hahn et al. ............ 424/401
6,241,993 B1 * 6/2001 Breton et al. ............. 424/401

FOREIGN PATENT DOCUMENTS

| EP | 0 680 749 A2 | 11/1995 |
| FR | 2 738 485 A1 | 3/1997 |
| WO | WO 01 13877 A1 | 3/2001 |

OTHER PUBLICATIONS

Roberts et al. Agents Actions 37: 53-59, 1992.*
Rains C et al. Drugs Aging. 7: 317-28, 1995.*
Green et al. J Toxicol—Cut Ocular Toxicol 14: 23-48, 1995.*
Jourdain et al. Contact Dermatitis, 46: 162-169, 2002.*
Trevisani M et al. Ethanol elicits and potentiates nociceptor responses via the vanilloid receptor-1. Nat Neurosci. Jun. 2002; 5(6):546-551, e-date: May 7, 2002.*
Robinson et al., "Evaluation of a Quantitative Clinical Method for Assessment of Sensory Skin Irritation", Contact Dermatitis, Munksgaard Oct. 2001, vol. 45, No. 4, pp. 205-213, Denmark.
French Search Report Issued in French Priority Counterpart FR/02/07869 Issued Mar. 28, 2003—2 Pages.
French Search Report Issued in French Priority Counterpart FR/02/07895 Issued Feb. 25, 2003—2 Pages.

* cited by examiner

*Primary Examiner* — Elizabeth C Kemmerer
*Assistant Examiner* — Kimberly A Ballard
(74) *Attorney, Agent, or Firm* — Buchanan Ingersoll & Rooney PC

(57) ABSTRACT

The invention relates to new non-therapeutic methods allowing the level of skin neurosensitivity and/or the state of neurosensorial skin reactivity of an individual to be evaluated by applying a peripheral nervous system stimulant to one skin area, the method being implemented under conditions of safety and comfort acceptable for the user, irrespective of his or her skin type.

35 Claims, 4 Drawing Sheets

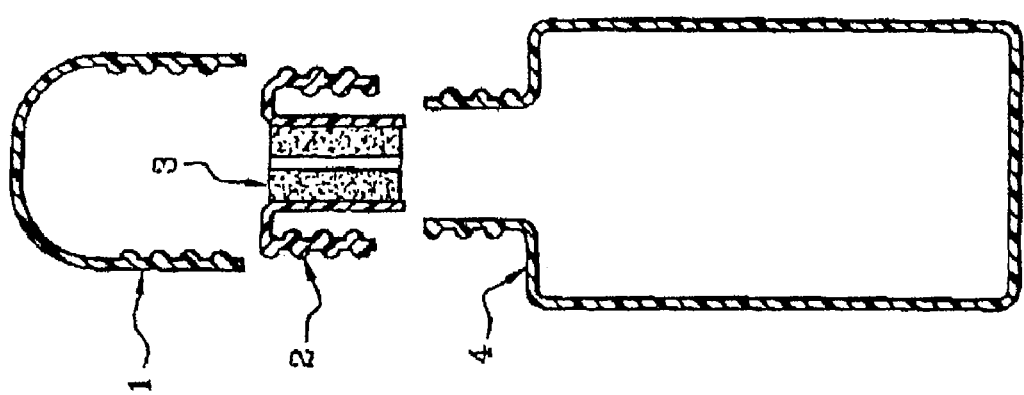
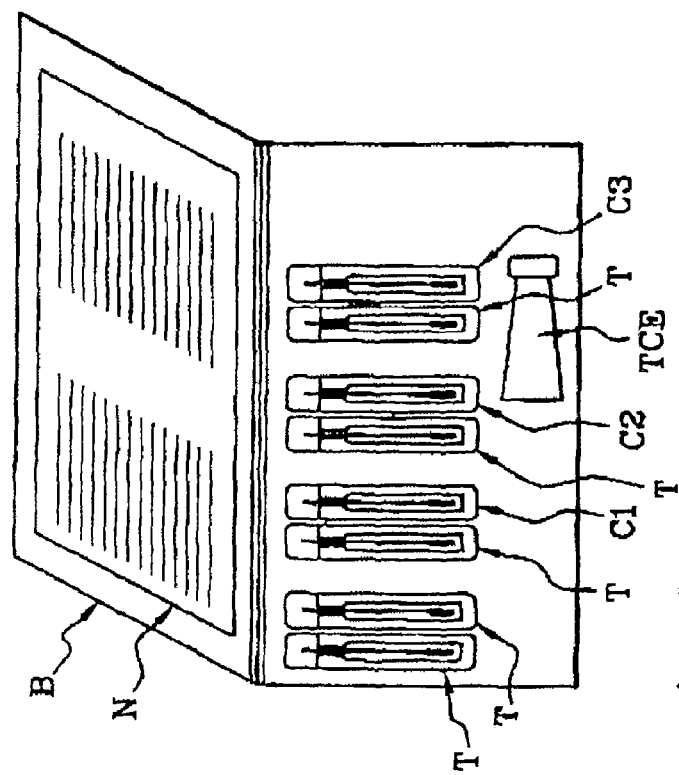

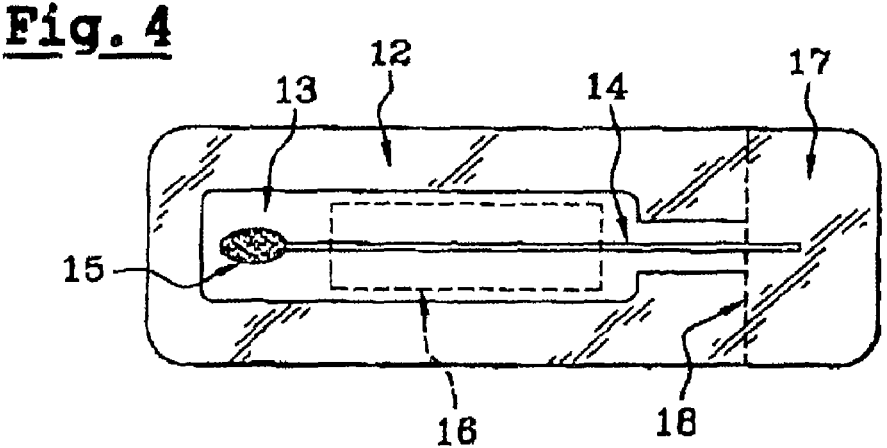
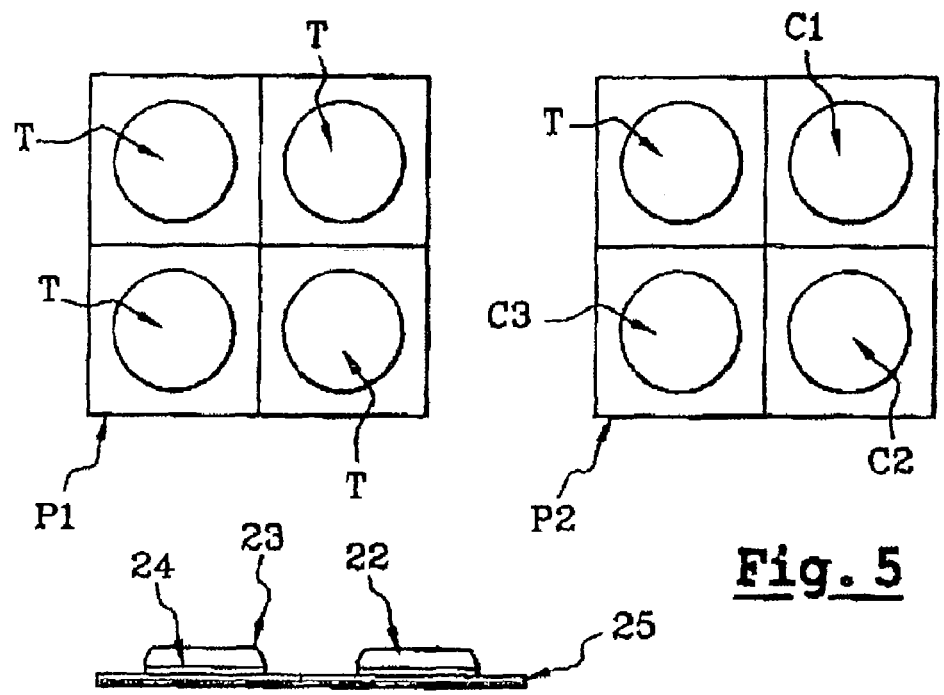

NON-THERAPEUTIC METHODS OF EVALUATING SKIN NEUROSENSITIVITY, KIT AND USE OF A KIT FOR IMPLEMENTING THE METHOD

CROSS-REFERENCE TO PRIORITY/PROVISIONAL APPLICATIONS

This application claims priority under 35 U.S.C. §119 of FR-02/07869, filed Jun. 25, 2002, FR-02/07895, filed Jun. 25, 2002, and of provisional applications Ser. No. 60/395,349, filed Jul. 12, 2002, and No. 60/395,353, also filed Jul. 12, 2002, all hereby expressly incorporated by reference. This application is also a continuation of said '349 and '353 provisionals.

BACKGROUND OF THE INVENTION

Technical Field of the Invention

The invention relates to new non-therapeutic methods allowing the level of skin neurosensitivity and/or the state of neurosensorial skin reactivity of an individual to be evaluated by applying a peripheral nervous system stimulant to one skin area, the method being implemented under conditions of safety and comfort acceptable for the user, irrespective of his or her skin type.

Experience shows that consumers do not always make the best choice of cosmetic or skincare products, since they lack precise knowledge of their skin type and of its specific needs. This is particularly true for what are termed sensitive skins, for which the capacity for self-evaluation is very limited.

Consequently there exists a need to allow the level of skin neurosensitivity to be determined, since better knowledge of the level of skin neurosensitivity can guide consumers in the choice of products which are appropriate for them, or can guide the formulator in the preparation of targeted, or even personalized, products.

It is known that certain people have a very low level of skin neurosensitivity and react to irritant substances or to environmental factors (pollution, sun, seawater, dry cold) much more intensely than other people whose level of skin neurosensitivity is much higher; this is particularly the case for those persons said to have sensitive or reactive skins.

Skin neurosensitivity, especially sensitive or reactive skin, is not a pathological condition, but corresponds to a parameter which expresses a constitutional condition of the skin. Skin neurosensitivity is a constitutional condition of the skin in the same way as greasy skin or dryness, for example.

Sensitive skin is defined as skin which is hyper-reactive to various factors acting by non-immunological mechanisms. This hyperreactivity can be thought of as a lowering of the skin's tolerance threshold to stimuli which are normally well tolerated. These stimuli are external in origin, and physical or chemical in nature. In the language of the consumers, the terms "sensitive skin" and "reactive skin" are virtually equivalent, and are considered to be synonymous; it is therefore possible to refer without distinction to sensitive skin or reactive skin.

Several decades after the first publications relating to sensitive skin, the point of consensus on which the majority of authors are agreed is the authenticity of this syndrome. It is interesting to note that the works of dermatology never refer to "sensitive skin" or to any equivalent clinical syndrome, clearly revealing the cosmetic character of this entity. It is this that may underlie the lack of understanding of this syndrome among a large section of the dermatological world.

Epidemiological studies carried out in Europe and the United States find equivalent frequencies. Approximately half of women and a third of men state that they have sensitive skin; 10% of women and 6% of men state that they have highly sensitive skin. With increasing age, the frequency of sensitive skin tends to diminish.

The greater frequency of sensitive skin among women explains why the majority of the studies relating to sensitive skin have been devoted to them.

Individuals with sensitive skin complain in the first place of symptoms of skin discomfort. This "skin discomfort" is manifested in neurosensorial signs which are sensations of hotness, stinging, pins and needles or itching. In the very great majority of the cases these symptoms are strictly localized on the face. Nevertheless, around 25% of men and women complain of having a sensitive scalp. In certain individuals the sensitive hyperreactivity may extend to other areas of the body, but always in association with the attacking of the face, which remains preponderant.

The onset of these symptoms is triggered by a number of types of factor. The factors involved may be environmental (changes in temperature, heat, cold, wind, sun, atmospheric pollution, etc.) or may involve the application of certain topical products, "hard" water (with a high concentration of calcium) or else may be internal factors (emotional factors, menstrual cycles, dietary factors, etc.).

The etymological relationship between the terms "sensitive" and "sensitization" must certainly be taken into account in the confusion which still reigns between "allergic skins" and "sensitive skins". As early as 1962, H. Thiers (Peau sensible [Sensitive skin] in: Thiers Héd. Les cosmétiques, 2nd ed., Paris: Masson, 1986: 266-8) indeed emphasized that sensitive skins were not linked to an immunological manifestation.

The applicant has shown that the intensity of the manifestations and the factors of reactivity vary from one subject to another, and enabled a number of clinical forms to be described.

Highly Sensitive Skins:

These concern approximately 10% of women and 6% of men. These highly sensitive skins are expressed in a very high reactivity of the skin of the face both to topical products and to environmental factors (including atmospheric pollution) and also to internal factors such as stress or conditions of fatigue. Among highly sensitive skins, both dry skins and greasy skins are encountered.

These highly sensitive skins may present crisis conditions which may extend over periods of several days, or even several weeks. During these crisis periods skin hyperreactivity is extreme, with the skin becoming intolerant to any epicutaneous application, including that of products which are customarily well tolerated in a normal period. This state of extreme skin intolerance, or "status cosmeticus", is manifested in the appearance of all of the signs of discomfort associated with an erythema as soon as a product is applied to the skin. These states of skin intolerance are often highly disconcerting for patients and dermatologists.

Environmental Sensitive Skins:

Approximately 15 to 20% of women present a sensitive skin which reacts principally to environmental factors such as heat or sharp changes in temperature. Women with this type of sensitive skin often have a porcelain appearance to their skin and sometimes complain of intolerance to the sun; however, although their complexion is rather light, it seems to be a question more of sensitivity to heat than of sensitivity to ultraviolet rays. It is among these sensitive skins that dry skins and skins which redden easily are most frequently encountered.

Cosmetic Sensitive Skins:

Approximately 25% of women present sensitive skin which reacts principally to epicutaneous applications. The trigger factor here is primarily the application of products which contain an active ingredient which is poorly tolerated in these persons. It is important to specify that this intolerance, the source of skin discomfort which is sometimes (but not always) associated with a redness, does not fall within the scope of an allergic mechanism. The appearance of the state of skin discomfort follows immediately or within minutes following the application of the product, and does so right from the first application. It should be underlined that this state is also quite different to the conditions of extreme intolerance of the "status cosmeticus", the intolerance here being limited to a single product or a small number of products which are readily identifiable.

Techniques for evaluating skin reactivity which use irritants are already known.

Mention may be made of the lactic acid test, or stinging test, which is described by Frosch P. J., Kligman A. M., in the document J. Soc. Cosmet. Chem., 1977, 28: 197-209.

This test, which is performed on the nasogenial sulcus, consists in quantifying the stinging which appears following the application of a 10% lactic acid solution. The protocol most commonly used at present consists in evaluating the stinging every minute on a scale from 0 to 3 for 5 minutes, making reference to the opposite side, which serves as a control, to which the vehicle solution is applied. The final score is as follows: (sum of the scores on the lactic acid side−sum of the scores on the control side). However, the diagnostic character of the test is not generally agreed on, since not all the "stingers" are persons with sensitive skin (see the document Contact Dermatitis, 1998, 38: 311-315).

Furthermore, EP-0-680,749 A2 describes a test with capsaicin for characterizing people with sensitive skin by virtue of the neuro-sensorial response induced by cutaneous application of capsaicin. Persons with sensitive skin show, in effect, levels of skin discomfort which are greater than in those having non-sensitive skin following application of a capsaicin cream. This test consists in applying to approximately 4 cm$^2$ of skin 0.05 ml of a cream containing $7.5 \times 10^{-2}$% of capsaicin and in recording the appearance of subjective signs provoked by this application, such as stinging, burning and itching. In contrast to the lactic acid test, this test has a predictive character for the diagnosis of sensitive skin.

This test certainly represents an improvement in the diagnosis of sensitive skin, but still has drawbacks. Thus the test takes a long time to implement (approximately 30 minutes) and cannot be used in practice, simply, by consumers for self-diagnosis of their own sensitive skin. Moreover, the test described in EP-0-680,749 A2 necessarily involves using a cream of which the amount to be applied must be quantified using a 1 ml syringe, and the application of the cream over a very precise area of the skin. In fact, the practical performance of this test necessitates the presence of an experimental technician to perform the test on a person.

The protocol of the test of EP-0-680,749 A2 is therefore difficult to implement by an unskilled person, and consequently it is particularly unsuitable for use by a consumer in self-diagnosis.

Likewise known is a technique which allows a correlation to be made between the response profile concerning the self-perception of sensations and the thresholds of detection of capsaicin (B. G. Greene et al., *J. Soc. Cosmet. Chem.,* 43, 131-147, 1992). With this technique, the subjects tested place the perceived skin sensations on a scale (no sensation, barely detectable, slight, moderate, strong, very strong, the strongest imaginable) of the sensations they sense following hypothetical skin stimuli which are provided in a questionnaire. The study continues on the same subjects by iterative applications of increasing amounts of capsaicin until the subject under test feels moderate or strong sensations.

Mention may also be made of the document Chemical Senses, 13(3), 367-384, 1988, which studies the nature and intensity of the sensations induced by the topical application of aqueous-alcoholic solutions of capsaicin to the forearm. The aim of this study is to determine an overall level of sensitivity to capsaicin by applying increasing concentrations of capsaicin to the subjects (a single concentration is tested per day). The technique described necessarily involves the application of a first concentration of capsaicin of 0.05%.

However, the implementation of the prior art techniques is inappropriate in those people who have a low level of skin neurosensitivity, who are the central target for products for sensitive skin. This is because, with these techniques, the concentrations of irritant (capsaicin) used immediately provoke in such persons pain sensations and/or reactions of irritation which are often intolerable. This is particularly the case with those individuals unaware that they present, constitutionally, a particularly low skin neurosensitivity threshold.

The invention is aimed at further increasing the diversity of the methods and devices available to the public and professionals for evaluating the level of skin neurosensitivity in an individual, particularly the condition of the skin reactivity or sensitive skin, at making the said methods sufficiently simple and quick to implement, and at allowing their use on a large scale.

Surprisingly and unexpectedly the Applicant has now discovered new non-therapeutic methods for evaluating skin neurosensitivity, in particular the condition of skin reactivity or sensitive skin, the said evaluation being performed:

(i) either by single topical application to the skin of a vehicle comprising a concentration of a peripheral nervous system stimulant, with deduction of information regarding the skin reactivity or sensitivity of an individual as a function of the intensity of the unattractive sensations capable of being perceived by the said individual;

(ii) or by successive applications of a vehicle comprising increasing concentrations of peripheral nervous system stimulant until a sensation, however small, is perceived by the subject or else until a maximum concentration which has not induced any sensation has been applied, the test reaching its end at this stage, well before being within the pain register.

Accordingly, the methods of the invention are compatible with a cosmetic diagnostic tool since they are carried out under conditions of comfort acceptable by any type of individual, without any pain being perceived during implementation and under conditions of total safety and without giving rise to side-effects.

Moreover, the methods of the invention according to (i) are easier to implement, more discriminating and more precise than the known, prior-art tests and so make it possible to improve the identification of people having sensitive or reactive skin. The techniques according to the present invention are particularly suitable for use by consumers in self-diagnosis.

BRIEF DESCRIPTION OF THE DRAWINGS

FIG. 2 is an illustrate of an exemplary bottle.

FIG. 3 is an illustrate of an exemplary single-use kit.

FIG. 4 is an illustrate of an exemplary single-dose unit.

FIG. 5 is a diagrammatical showing of an exemplary two platelets kit.

Figure 1:
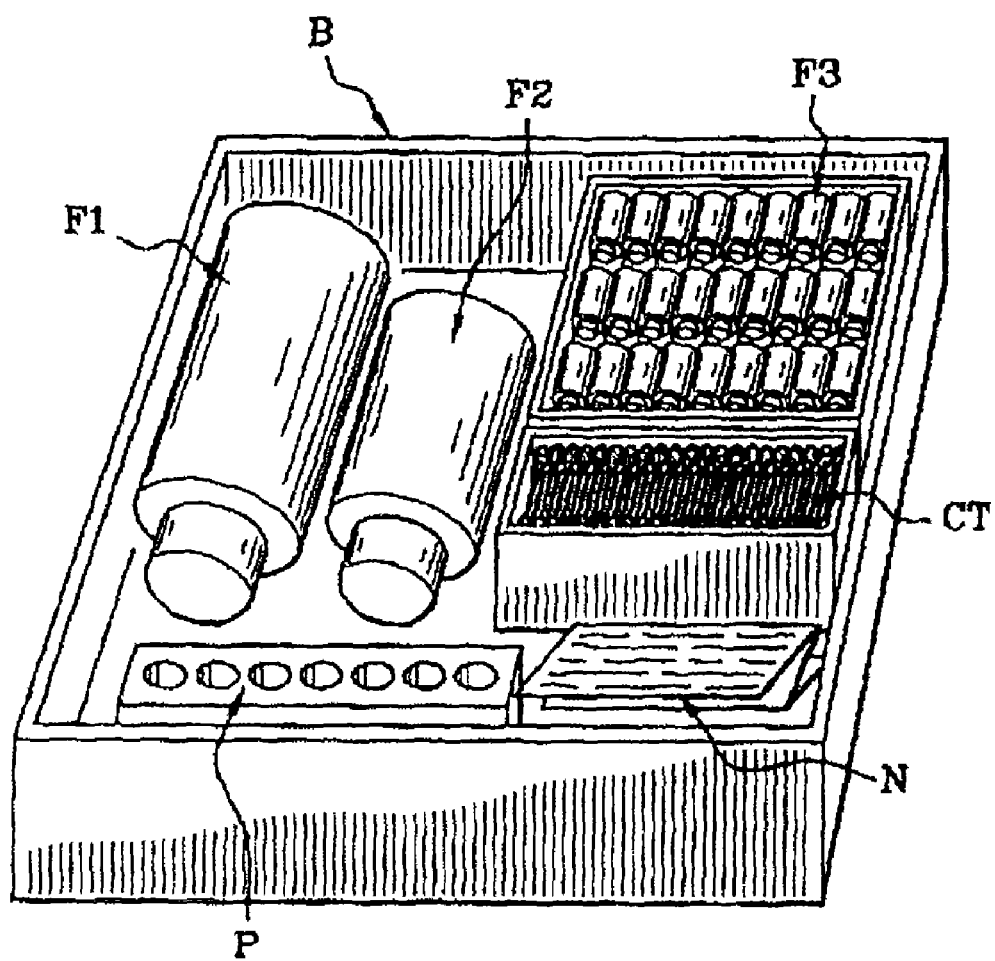
FIG. 1 is an illustrate of an exemplary assembly for production of multi-use kits.

The invention provides in particular a non-therapeutic method of evaluating the level of skin neurosensitivity of an individual, which comprises:

1) applying to a skin area of the said individual a composition comprising a physiologically acceptable vehicle and a peripheral nervous system stimulant, the concentration of the said stimulant being between $1 \times 10^{-6}$ and $5 \times 10^{-4}\%$ by weight relative to the total weight of the composition;
2) recording whether the individual detects or perceives an unattractive sensation and deducing therefrom information regarding the skin neurosensitivity of the individual, advantageously the skin reactivity or sensitivity.

In a first preferred embodiment the invention provides a non-therapeutic method of identifying persons having sensitive skin, which comprises:

1) applying to a skin area of an individual, advantageously the bend of the arm, the lobe of the ear or the posterior face of the pinna of the ear or the face, in particular the wing of the nose or the nasogenial sulcus, an aqueous or aqueous-alcoholic solution, advantageously an aqueous-ethanolic solution, containing from 1% to 50% of ethanol in water, advantageously from 5% to 20%, preferably 10% of ethanol, of an agent selected from capsaicinoids and mustard oil at a concentration of between $1 \times 10^{-6}$ and $5 \times 10^{-4}\%$, advantageously between $5 \times 10^{-5}$ and $5 \times 10^{-4}\%$; preferably the concentration is $1 \times 10^{-4}\%$; and
2) deducing information regarding the skin reactivity or sensitivity of an individual as a function of the intensity of the unattractive sensations capable of being perceived by the said individual.

Advantageously, in accordance with the first embodiment of the invention, step 1) comprises between 1 and 3 applications of the solution, preferably 3 applications.

The aqueous-alcoholic capsaicin solution is applied by way of a single applicator system, in particular using cotton buds or a piece of cotton (of the circular type for makeup removal) folded into 4.

The percentages given correspond to the percentage by weight relative to the total weight of the composition.

Advantageously, step 1) of the method according to the first embodiment is preceded by a step 0) which consists in applying to a skin area of an individual, advantageously the bend of the arm, the lobe of the ear or behind the pinna of the ear or the face, in particular to the wing of the nose or the nasogenial sulcus, a solution of lactic acid at a concentration of between 2% and 10%, advantageously 10%. Accordingly, a preferred non-therapeutic method of identifying persons having sensitive skin comprises:

0) applying to a skin area of an individual, advantageously the bend of the arm, the lobe of the ear or behind the pinna of the ear or the face, in particular to the wing of the nose or the nasogenial sulcus, a solution of lactic acid at a concentration of between 2% and 10%, advantageously 10%; then
1) applying to a skin area of the same individual, advantageously the bend of the arm, behind the lobe or the face, in particular to the wing of the nose or the nasogenial sulcus, an aqueous or aqueous-alcoholic solution, advantageously an aqueous-ethanolic solution, containing from 1% to 50% of ethanol in water, advantageously from 5% to 20%, preferably 10% of ethanol, of an agent selected from capsaicinoids and mustard oil at a concentration of between $1 \times 10^{-6}$ and $5\% \times 10^{-4}\%$, advantageously between $5 \times 10^{-5}$ and $5 \times 10^{-4}\%$; preferably the concentration is $1 \times 10^{-4}\%$; and
2) deducing information regarding the skin reactivity or sensitivity of an individual as a function of the intensity of the unattractive sensations capable of being perceived by the said individual.

Advantageously, step 0) comprises between 1 and 10 applications of lactic acid solution, advantageously 10 applications.

Advantageously, step 1) comprises between 1 and 3 applications of the agent, advantageously 3 applications.

The two aforementioned methods have the advantage that they can be easily and quickly implemented at an industrially acceptable cost while at the same time allowing sufficiently precise and rapid information to be obtained in order to allow easy diagnosis of the existence of a condition of sensitive or reactive skin.

Furthermore, both of these aforementioned methods allow diagnosis of a condition of skin reactivity or sensitive skin in an individual and differ from each other only in the use of a solution of capsaicin alone or of a solution of lactic acid and then a solution of capsaicin: the first method is easier to use, the second method is more discriminating and precise.

In a second preferred embodiment, the invention provides a non-therapeutic method of evaluating the level of skin neurosensitivity of an individual, which comprises:

1) applying to a skin area of the said individual a first composition comprising a physiologically acceptable vehicle and a peripheral nervous system stimulant, the concentration of the said stimulant being between $1 \times 10^{-6}$ and $1 \times 10^{-4}\%$ by weight;
2a) recording whether the individual detects an unattractive sensation;
2b) if no sensation is detected by the individual, repeating steps 1) and 2a) with a composition containing a higher concentration of the same stimulant until the individual detects an unattractive sensation or until a composition containing a maximum concentration value of the said stimulant is applied;
2c) deducing, from the last concentration applied, information regarding the skin neurosensitivity of the individual.

Advantageously, in accordance with this second embodiment of the invention, the concentration of the stimulant in the composition which is applied in step 2b) is such that its application is unlikely to give rise to painful unattractive sensations in the individual. Preferentially the concentration of the stimulant in the composition which is applied in step 2b) increases by a factor of between 1.5 and 10, preferably by a factor of between 2 and 5, and advantageously it increases by a factor of the square root of 10.

In the method according to the second embodiment of the invention, the maximum concentration value of peripheral nervous system stimulant which can be applied is $1 \times 10^{-2}\%$ by weight.

According to the invention, when compositions are applied successively, it is understood that substantially the same volume or the same quantity of said compositions will be applied to substantially the same skin area.

A physiologically acceptable vehicle is a vehicle which is compatible with the skin, mucosae, nails and hair. Moreover, this vehicle is appropriate for the application of the peripheral nervous system stimulant and permits ready bioavailability of the said stimulant following topical application to the skin, without this vehicle itself being a peripheral nervous system stimulant.

The vehicles according to the invention correspond to pharmaceutical forms which are well known to the person skilled in the art. These vehicles may be present in any of the pharmaceutical forms normally used for topical application: they may in particular be aqueous, aqueous-alcoholic or oily solutions, dispersions of the lotion or serum type, anhydrous or lipophilic gels, emulsions of liquid or semi-liquid consistency of the milk type, obtained by dispersing a fatty phase in an aqueous phase (O/W) or inversely (W/O), or suspensions or emulsions of soft, semi-solid or solid consistency, or else microemulsions, microcapsules, microparticles or vesicular dispersions of ionic and/or nonionic type, advantageously solutions, preferably aqueous-alcoholic solutions with an alcohol content of less than 50%. These compositions are prepared in accordance with the usual techniques.

The peripheral nervous system stimulant is an agent which induces a sensorial response linked to the deployment of sensitive skin nerves whose ends emerge within the stratum corneum.

The peripheral nervous system stimulant is a substance capable of inducing an unattractive sensation when applied topically to the skin. Moreover, the said agent is capable of inducing release of substance P and/or of CGRP (Calcitonin Gene Related Peptide) when applied topically to the skin. These peptides may be released by reaction with monoclonal antibodies in the case of substance P (in accordance with a technique described by Cuello et al. in Proc. Natl. Acad. Sci. USA 1979; 76: 3532-6) or by the radioimmunoassay technique for substance P and CGRP (technique described by Wallendren et al. in Acta Derm. Verereol. 1987; 67: 185-92), this second technique being particularly suitable for the skin.

A peripheral nervous system stimulant is selected advantageously from natural and synthetic capsaicinoids, preferably capsaicin, homocapsaicin, homodihydrocapsaicin, nordihydrocapsaicin, dihydrocapsaicin, advantageously capsaicin; lactic acid, glycolic acid, ethanol at a concentration of more than 50%, and mustard oil.

Advantageously the concentration of the first composition applied is between $1\times10^{-6}$ and $1\times10^{-4}$%, more advantageously between $3\times10^{-6}$ and $6\times10^{-5}$%; preferably $3.16\times10^{31\ 5}$%.

Advantageously, the skin area according to the invention is the bend of the arm, the lobe of the ear or the face, in particular the wing of the nose, the nasogenial sulcus or the point of the lower maxillary.

When the peripheral nervous system stimulant is capsaicin, a preferred vehicle is an aqueous-alcoholic solution, advantageously an aqueous-ethanolic solution, containing from 1% to 50% of ethanol in water, advantageously from 5% to 20%, preferably from 8% to 15% and more preferably 10%. These aqueous-ethanolic solutions of capsaicin are particularly stable over time for capsaicin concentrations of between $1\times10^{-2}$% and $1\times10^{-6}$%

For the purposes of the present invention an unattractive sensation is the smallest painless sensation perceived within an area treated by the stimulant which produces stinging, pins and needles, itching or pruritus, hotness, pulling and/or any other inconvenience or discomfort such as a sensation of blocking and/or vibrations. An unattractive sensation of this kind is detectable by an individual following application of a composition comprising the peripheral nervous system stimulant at a concentration of between $1\times10^{-6}$ and $1\times10^{-4}$% by weight.

The concentration of the first composition (called attack concentration) which contains the peripheral nervous system stimulant and which is used in the technique according to the invention has been determined beforehand to induce only unattractive sensations in persons having the highest degree of skin neurosensitivity.

This first concentration (optimum attack concentration) has been determined using as the vehicle an aqueous-ethanolic solution with an ethanol content of 10% (Example 1).

Capsaicin is the reference substance which is used as peripheral nervous system stimulant. Capsaicin is the principal hot substance in peppers. The hotness of a substance can be estimated by means of the Scoville test. This test establishes that pure capsaicin has the highest Scoville rating (16 million Scoville units) of all known hot substances that have been tested. Consequently, it will be appreciated that other peripheral nervous system stimulants can be used at the same attack concentration as capsaicin (between $1\times10^{-6}$ and $1\times10^{-4}$%, advantageously between $3\times10^{-6}$ and $6\times10^{-5}$%; preferably $3.16\times10^{-5}$%) without immediately giving rise to pain sensations.

The percentages given correspond to the percentage by weight relative to the total weight of the composition.

According to the invention, the final concentration tested in step 2b) can correspond to the maximum concentration or to the concentration which has given rise to the said unattractive sensation.

In another embodiment, the method according to the invention comprises, before step 1), the prior application to a skin area of a composition comprising the vehicle without stimulant. In another embodiment of the invention, the method comprises, before step 1), the prior application to a skin area and to its area on the opposite side of a composition comprising the vehicle without stimulant.

In one preferred embodiment of the invention the non-therapeutic method comprises the following successive steps:
a1) applying a composition containing the vehicle to a skin area;
b1) recording whether the subject perceived an unattractive sensation on the skin area having received the vehicle;
c1) if so, stopping the test; if not, applying to a skin area, preferably to the same area having received the vehicle previously, the same vehicle containing the said stimulant at a concentration of between $1\times10^{-6}$ and $1\times10^{-4}$%;
d1) recording whether the subject perceived an unattractive sensation on the skin area having received the composition containing the stimulant;
e1) if so, recording the concentration of stimulant and stopping the test; if not, increasing the concentration of stimulant by a factor of between 1.5 and 10, and repeating steps c1) to e1) n times, where n is between 1 and 10.

It is advantageous, following step a1) and before step b1) and/or following step c1) and before step d1), to wait for 30 to 360 seconds, preferably from 120 to 200 seconds, particularly for 180 seconds.

In another preferred embodiment of the invention the non-therapeutic method comprises the following successive steps:
a2) applying a composition containing the vehicle to a skin area and to its area on the opposite side;
b2) recording whether the subject perceived an unattractive sensation on at least one of the areas of the face having received the vehicle;
c2) if so, stopping the test; if not, applying to a skin area, the same vehicle containing the said stimulant at an attack concentration of between $1\times10^{-6}$ and $1\times10^{-4}$%; and applying the same vehicle to the area on the opposite side;
d2) recording whether the subject perceived a discriminating unattractive sensation on the skin area having received the vehicle containing the stimulant in relation to the skin area on the opposite side;

e2) if so, recording the concentration of stimulant and stopping the test; if not, increasing the concentration of stimulant by a factor of between 1.5 and 10, and repeating steps c2) to e2) n times, where n is between 1 and 10.

It is advantageous, following step a2) and before step b2) and/or following step c2) and before step d2), to wait for 30 to 360 seconds, preferably from 120 to 200 seconds, particularly for 180 seconds.

According to the invention, when compositions are applied successively on the same skin area, said skin area can be cleaned before a subsequent application.

The techniques according to the second embodiment of the invention have the advantage of being easy and quick to implement at an industrially acceptable cost while at the same time allowing sufficiently precise and rapid information to be obtained in order to allow easy diagnosis of the degree of skin neurosensitivity. The techniques according to the second embodiment of the invention have the additional advantage of showing good repeatability, in the clinical sense of the term.

The invention further provides methods of cosmetic treatment of the skin of an individual which comprise any one of the methods already described and a step which comprises cosmetically treating the skin with a cosmetic product as a function of the skin neurosensitivity evaluated.

In order to understand what is meant by "cosmetic" in the sense of the present invention reference may be made to the Cosmetics Directive 76/768/EEC.

A "cosmetic treatment" is any non-therapeutic treatment by means of a cosmetic product as defined in the above Directive.

The invention further provides methods of determining the effectiveness of a cosmetic treatment able to act on the skin neurosensitivity of an individual, which comprise any one of the methods described beforehand, cosmetically treating the skin with a cosmetic product as a function of the skin neurosensitivity evaluated, repeating on the treated skin any one of the methods described above, then deducing, from a comparison of the results before and after treatment, an indication relative to the effectiveness of the cosmetic treatment.

The invention further provides a kit comprising:
a plurality of containers each holding increasing concentrations of peripheral nervous system stimulant in combination with a vehicle,
at least one container which holds the vehicle alone, and
single applicator systems, preferably cotton buds, characterized in that at least one container holds a concentration of peripheral nervous system stimulant of between $1\times10^{-6}$ and $1\times10^{-4}$% by weight, advantageously between $3\times10^{-6}$ and $6\times10^{-5}$%; preferably $3.16\times10^{-5}$% by weight relative to the total weight of the composition.

In the kit, the peripheral nervous system stimulant and the vehicle have the same definitions as those described earlier.

A container in the sense of the present invention is any kind of vessel of whatever form. By way of non-limiting example it may be a pot, a bottle, a flask, a sachet, a tube or a capsule.

Advantageously the kit comprises
one or more sets of 3 to 6 containers holding, respectively, stimulant concentrations selected from $3.16\times10^{-5}$% (C1), $1\times10^{-4}$% (C2), $3.16\times10^{-4}$% (C3), $1\times10^{-3}$% (C4), $3.16\times10^{-3}$% (C5) and $1\times10^{-2}$% (C6), in a vehicle,
a container holding the vehicle alone, and
cotton buds, with the proviso that the kit comprises at least one container with an attack concentration of between $1\times10^{-6}$ and $1\times10^{-4}$%, advantageously between $3\times10^{-6}$ and $6\times10^{-5}$%; preferably $3.16\times10^{-5}$%.

In one version the kit comprises:
a container holding a stock solution of stimulant at a concentration of $1\times10^{-2}$% in a vehicle,
at least one container holding the vehicle alone,
at least one empty container;
a note containing use instructions for the preparation and bottling of selected solutions $C_1$-$C_6$ as defined above; with the proviso that the use instructions comprise the production of at least one container with an attack concentration of between $1\times10^{-6}$ and $1\times10^{-4}$%, advantageously between $3\times10^{-6}$ and $6\times10^{-5}$%; preferably $3.16\times10^{-5}$%.

Advantageously the kit further comprises an emollient cream for treating the area of application.

Advantageously the kit further comprises a set of kit instructions including the major points of one of the protocols as described above, advice and conclusions to be given to the person on the choice of a cosmetic product and/or recommendations on his or her cosmetic practices and actions, as a function of his or her skin neurosensitivity thus evaluated.

The invention further provides for the use of the kit in any one of the evaluation methods described earlier.

In order to further illustrate the present invention and the advantages thereof, the following specific examples are given, it being understood that same are intended only as illustrative and in nowise limitative.

EXAMPLE 1

Determination of the Attack Concentration and Optimum Concentration Step with an Aqueous-alcoholic Solution of Capsaicin:

The aim of this study was to set an optimum initial concentration for the beginning of the test that does not induce pain and to fix a concentration step sufficiently large not to excessively increase the number of successive steps and sufficiently small that, at the concentration n+1, the test is not painful where unattractive sensations were not perceived at step n.

Capsaicin Solutions:
Capsaicin was tested in the form of aqueous-alcoholic solutions (ethanol 10%, water 90%).

Experimental Design:
Randomized, single-blind study, controlled
13 healthy subjects of both sexes
4 capsaicin solutions tested: $3.3\times10^{-5}$% (C1), $1\times10^{-4}$% (C2), $3.3\times10^{-4}$% (C3), $1\times10^{-3}$% (C4)

1st step: Simultaneous application to the nasogenial sulci on each side of the face of the vehicle, using impregnated cotton buds, in order to acclimatize the volunteer to the sensations induced by application of the vehicle. Waiting time of 3 minutes.

2nd step: Application of the vehicle to one side and of the capsaicin solution at concentration C1 on the other. After 3 minutes, ask whether the subject has perceived a difference between the 2 sides. If the subject describes an unattractive sensation on the side which has received the capsaicin, stop the test and allocate C1 as the detection threshold. If not, go immediately to step 3.

3rd step: Application of solution C2 to the side which has received the vehicle in step 1 and of the vehicle to the other side. After 3 minutes, ask whether the subject has perceived a difference between the 2 sides. If the subject describes a particular sensation on the side which has received the capsaicin, stop the test and allocate C2 as the detection threshold. If not, go immediately to step 4.

4th step: Application of solution C3 to the side which has received the vehicle in step 2 and of the vehicle to the other side. After 3 minutes, ask whether the subject has perceived a difference between the 2 sides. If the subject describes a particular sensation on the side which has received the capsaicin, stop the test and allocate C3 as the detection threshold. If not, go immediately to step 5.

5th step: Application of solution C4 to the side which has received the vehicle in step 3 and of the vehicle to the other side. After 3 minutes, ask whether the subject has perceived a difference between the 2 sides. If the subject describes a particular sensation on the side which has received the capsaicin, allocate C4 as the detection threshold. If not, allocate as the detection threshold: concentration>C4.

Duration of the test: Initial explanations+5 steps of 3 to 4 minutes each, with a maximum test duration of 20 to 25 minutes for subjects continuing through to the final step.

Results:

The information collected from the subjects concerning their evaluation of the test reveals that the test was absolutely painless for all of the 13 subjects and that the concentration step is sufficiently low to prevent a painful sensation with the concentration $C_{n+1}$ when a subject has not perceived an unattractive sensation beforehand at $C_n$.

Conclusions:

The results of this test thus allow an optimum attack concentration of $$\sqrt{10} \times 10^{-5}\%$$

and an appropriate inter-concentration step of $$\sqrt{10}$$

to be determined.

EXAMPLE 2

Embodiment Example of a Kit Serving for Detection of the Level of Sensitive Skin, the Kit Being Intended for an Advanced Professional User:

Assembly (see FIG. 1) allowing the production of 5 multi-use kits for use approximately 250 times, comprising in a box B the following elements:
1. a holder P allowing 7 bottles as described in section 4 of this list to be held upright;
2. a bottle F1 containing a 10% aqueous-alcoholic solution (for example, of 300 ml);
3. a bottle F2 containing a stock solution of capsaicin at $1\times10^{-2}\%$ (for example, of 100 ml) in a 10% aqueous-alcoholic solution;
4. 40 stoppered empty bottles F3 (for example, of 20 ml); a bottle F3 (see FIG. 2) is composed of a vessel 4 adapted to receive a first stopper 2 which allows spillages to be prevented and allows the cotton buds to be wrung out when solutions are withdrawn via a central foam part 3, cut out so as to allow the passage of a cotton bud, with a standard stopper 1 fitting the first stopper;
5. 600 standard cotton buds CT;
6. a usage note N containing the following elements: a) use instructions for preparing and bottling the solutions $C_1$-$C_5$ ($3.16\times10^{-5}\%$ (C1), $1\times10^{-4}\%$ (C2), $3.16\times10^{-4}\%$ (C3), $1\times10^{-3}\%$ (C4) and $3.16\times10^{-3}\%$ (C5)), comprising the following series of steps:
   fill a bottle F3T with 15 ml of the 10% aqueous-alcoholic solution of F1;
   fill a bottle F3 with 15 ml of solution from the bottle F2; number this bottle F3C6;
   draw 5 ml from this bottle F3C6 and transfer it to a second bottle F3C5; add 10 ml of the aqueous-alcoholic solution of F1 to F3C5;
   reproduce iteratively the above steps in order to obtain F3C1-4;
b) use instructions for the implementation of the test, reproducing the protocols of Example 1, using the cotton buds CT and the bottles F3C1-6 and F3T prepared above. The bottles must be stored at 4° C. between two instances of use and discarded after one week of use;
c) a calibration system (atlas) allowing interpretation of the results (C1: excessively sensitive skin; C2: highly sensitive skin; C3: moderately sensitive skin; C4: relatively insensitive skin; C5: virtually insensitive skin; C5 not detected: completely insensitive skin).

EXAMPLE 3

Embodiment Example of a Kit Serving for Detection of the Level of Sensitive Skin, the Kit Being Intended for an Institutional Professional User:

This kit allows approximately 50 instances of use and comprises in a box (B) the following elements:
1. a holder P allowing 7 bottles as described in section 2 of this list to be held upright;
2. 5 bottles F3 of 20 ml containing respectively 15 ml of solutions $C_1$-$C_5$ ($3.16\times10^{-5}\%$ (C1), $1\times10^{-4}\%$ (C2), $3.16\times10^{-4}\%$ (C3), $1\times10^{-3}\%$ (C4) and $3.16\times10^{-3}\%$ (C5)) and a bottle F3T containing 15 ml of a 10% aqueous-alcoholic solution T; these bottles are shown in FIG. 2 and correspond to those defined in section 4 of Example 2;
3. 80 standard cotton buds CT;
4. a usage note containing the following elements:
a) use instructions for the implementation of the test, reproducing the protocol of Example 1, using the cotton buds and the bottles F3C1-5 and F3T; the bottles must be stored at 4° C. between two instances of use and discarded after one week of use.
b) a calibration system (atlas) allowing interpretation of the results (C1: excessively sensitive skin; C2: highly sensitive skin; C3: moderately sensitive skin; C4: relatively insensitive skin; C5: virtually insensitive skin; C5 not detected: completely insensitive skin).

EXAMPLE 4

Embodiment Example of a Kit Serving for Detection of the Level of Sensitive Skin, the Kit Being Intended for a Traveling Professional User:

This single-use kit (see FIG. 3) comprises in a box B the following elements:
1. 4 pairs of single dose units M1-4 and M'1-4 containing respectively solutions $C_1$-$C_3$ and 10% aqueous-alcoholic solutions T in accordance with the presentation of FIG. 2, arranged as follows: per pair T/T (red label), T/C1 (orange label), T/C2 (yellow label) and T/C3 (green label). A single dose unit (represented in FIG. 4) is a thermoformed unit (blister) comprising an outer envelope 12 formed by two welded plastic films delimiting a central compartment 13 which contains a solution and an applicator system formed by a rod 14 and a tip 15. A label 16, which may be colored, is stuck to the outer part. In its lateral part 17, the outer envelope grips the distal part of the rod, with which it remains in one piece following the opening of the single dose unit by tearing of the outer envelope along the dashed line 18;
2. a tube of emollient cream (TCE), which soothes;
3. use instructions N printed on the cover, containing the following elements:
a) use instructions for the implementation of the test, reproducing the protocols of Example 1 using the single dose units M(')1-4. The emollient cream can be used after the test where the consumer describes discomfort. The kit must be thrown away after use.
b) a calibration system (atlas) allowing interpretation of the results (C1: excessively sensitive skin; C2: highly sensitive skin; C3: moderately sensitive skin; virtually or completely insensitive skin if C3 has not been detected).

EXAMPLE 5

Embodiment Example of a Kit Serving for Detection of the Level of Sensitive Skin, the Kit Being Intended for a Home User:

This single-use kit is identical in its functioning logic to that of Example 4. Transposition to home use is realized by means of a presentation form which ensures increased safety.

The kit is presented in the form of two "platelets" which are flexible and shown diagrammatically in FIG. 5. The first platelet P1 contains four control solutions T, the second platelet P2 contains four solutions T/C1/C2/C3. Each of these solutions 22 is contained in a depression 23, with a microporous gel 24 separating them from the surface. A protective paper film 24 ensures integrity in transit.

Furthermore, a calibration system (atlas) allowing interpretation of the results and the identification of the capsaicin solutions relative to the vehicle is provided in a closed envelope EF.

The two platelets P1 and P2 are mounted adhesively, symmetrically, on the two points on either side of the lower maxillary, following the removal of the protective film.

The test procedure is the same as that described above, except that contacting with the skin is carried out by pressing with the fingers on the two symmetrical depressions on either side of the face, which takes up the microporous gel.

If no dose is detected by an unattractive sensation, the subject is declared to have virtually or completely insensitive skin. If a dose is detected, the closed envelope EF is opened and, if the side corresponds to a concentration C1-3, the subject is declared to have, respectively, excessively sensitive skin, very sensitive skin or moderately sensitive skin.

EXAMPLE 6

Example of Information Regarding the Skin Neurosensitivity of the Individual as a Function of the Concentration (X) of the First Composition Detected by the Individual by an Unattractive Sensation, Which can be Given by the Following Correspondence Table:

| | |
|---|---|
| $1 \times 10^{-6}\% < X < 1 \times 10^{-4}\%$: | very high neurosensitivity |
| $1.5 \times 10^{-4}\% < x < 0.75 \times 10^{-3}\%$: | moderately high neurosensitivity |
| $1 \times 10^{-3}\% < X < 5 \times 10^{-3}\%$: | low neurosensitivity |
| $X > 1 \times 10^{-2}\%$: | very low neurosensitivity |

EXAMPLE 7

Use of the Kit of Example 3 to Determine the Skin Neurosensitivity Threshold of 150 Women:

Study performed in a single-blind procedure on a non-selective population of 150 women aged from 18 to 60 years living in Paris or the surrounding region.

Figure 6:
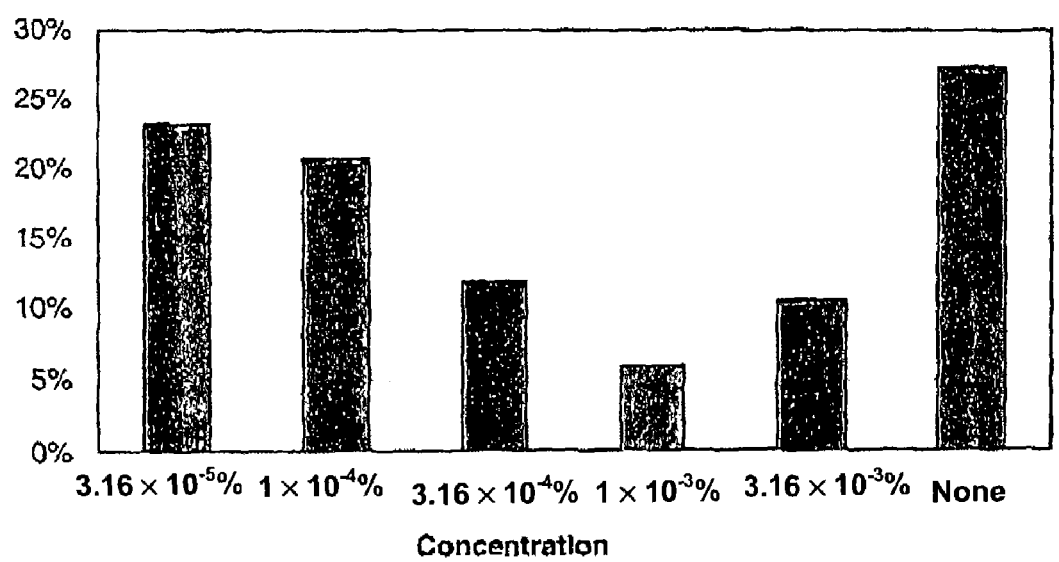
FIG. 6 is an exemplary histogram showing the incidence of the detection threshold.

Results:

FIG. 6 (FIG. 6) is a histogram showing the incidence of the detection threshold.

This graph shows that a number of levels of significantly distinct neurosensitivity exist in a non-selective population of 150 women aged from 18 to 60 years. Bear in mind that the concentrations of capsaicin are spaced apart by a factor of 3.16. This graph reveals two different populations: the subjects who detected C1, C2 or C3 (56%) form a "sensitive to highly sensitive" population; the subjects who detected C4 or C5 or who did not detect any concentration (44%) form a "virtually or completely insensitive" population.

It is interesting to note that the sensations reported at the level of the detection threshold (characterized by a sensation detected on the side where the capsaicin was applied, lasting for at least 30 seconds) are highly varied (presence, pins and needles, stinging, hotness, etc.)

The kinetics of the sensation were detailed for 74 of the 150 subjects:

| N | N Missing | Mean | Standard Deviation | Minimum | Maximum |
|---|---|---|---|---|---|
| 74 | 76 | 79.9 | 16.7 | 60 | 120 |

Overall and as a mean over 74 subjects, the delay before appearance is 79.9 seconds, or 1 minute 20 seconds.

Good Tolerance to the Test:

An essential point was to evaluate whether, at the concentration detected for the stopping of the test, the subject was able to perceive a significant discomfort.

The 109 women who detected a concentration were therefore asked to evaluate, on a scale from 1 to 5, the intensity of this sensation. Only those sensations at a level of 2 ("slight but perceptible"; 95%) and 3 ("moderately clearly perceptible"; 5%) were reported. No sensation of level 4 ("substantial") or ("painful") was reported.

This study demonstrates that the attack concentration and the plateaux are chosen judiciously for this Parisian population.

EXAMPLE 9

Non-therapeutic Method of Identifying Persons Having Sensitive Skin by Topical Application to the Skin of a Single Concentration of Capsaicin (Aqueous-ethanolic Solution of Capsaicin):

Experimental Design:
1) Apply 3 times in succession to the nasogenial sulcus an aqueous-ethanolic solution, with an ethanol content of 10%, of capsaicin at a concentration of $5 \times 10^{-4}\%$;
2) Record each minute for 5 minutes whether the person has perceived an unattractive sensation, on the nasogenial sulcus which has received the solution;
3) Assign a score for the unattractive sensation perceived on a scale of 0 to 3 (0: no sensation; 1: very slight sensation; 2: slight sensation; 3: moderate sensation);

4) The person is declared to have sensitive skin if the score is greater than or equal to 5 after 5 minutes or if a moderate sensation is perceived during the first three minutes.

EXAMPLE 10

Non-therapeutic Method of Identifying Persons Having Sensitive Skin by Topical Application to the Skin of a 10% Lactic Acid Solution and then a Single Concentration of Capsaicin (Aqueous-ethanolic Solution of Capsaicin):
Experimental Design:
a) Apply 10 times in succession to the nasogenial sulcus a solution of lactic acid at a concentration of 10%;
b) Record every minute for 5 minutes whether the person has perceived an unattractive sensation on the skin area which has received the solution;
c) Assign a score to the perceived unattractive sensation on a scale of 0 to 3 (0: no sensation; 1: very slight sensation; 2: slight sensation; 3: moderate sensation);
d) Pass to the following step if the score is greater than or equal to 5 after 5 minutes or if a slight or moderate or severe sensation is perceived during the first three minutes.
e) Apply 3 times in succession to the nasogenial sulcus an aqueous-ethanolic solution, with an ethanol content of 10%, of capsaicin at a concentration of $1 \times 10^{-4}\%$;
f) Record each minute for 5 minutes whether the person has perceived an unattractive sensation, on the skin area which has received the solution;
g) Assign a score for each unattractive sensation perceived on a scale of 0 to 3 (0: no sensation; 1: very slight sensation; 2: slight sensation; 3: moderate sensation);
h) The person is declared to have sensitive skin if the score is greater than or equal to 5 after 5 minutes or if at least one moderate sensation is perceived during the first three minutes.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A non-therapeutic method of evaluating the level of skin neurosensitivity of an adult individual to a capsaicinoid, the method comprising: 1) applying to a skin area of the individual a first composition comprising a physiologically acceptable vehicle that is an aqueous or aqueous-alcoholic solution and a peripheral nervous system stimulant that is a capsaicinoid, the concentration of the stimulant being between $1 \times 10^{-5}\%$ and $1 \times 10^{-3}\%$ by weight relative to the total weight of the composition; 2) recording whether the individual detects an unattractive sensation; 3) if no sensation is detected by the individual, repeating steps 1) and 2) with a composition containing a higher concentration of the same stimulant until the individual detects an unattractive sensation or until a composition containing a maximum concentration value of the stimulant is applied; and 4) deducing, from the last concentration applied, information regarding the skin neurosensitivity of the individual,
wherein the aqueous-ethanolic solution contains from 8% to 15% ethanol in water,
wherein the unattractive sensation perceived is scored on a scale of 0 to 5, wherein 0 represents no sensation, 1 represents very slight sensation, 2 represents slight sensation, 3 represents moderate sensation, 4 represents substantial sensation, and 5 represents painful sensation, and wherein an individual is declared to have sensitive skin if the score is greater than or equal to 5 after 5 minutes or if a moderate sensation is perceived during the first three minutes.

2. The method of claim 1, wherein the solution is an aqueous-ethanolic solution.

3. The method of claim 1, wherein the concentration of stimulant is between $5 \times 10^{-5}\%$ and $5 \times 10^{-4}\%$ by weight relative to the total weight of the composition.

4. The method of claim 3, wherein the concentration of the stimulant is $1 \times 10^{-4}\%$ by weight relative to the total weight of the composition.

5. The method of claim 1, wherein step 1) comprises between 1 and 3 applications of the aqueous-alcoholic solution to the skin area of the individual.

6. The method of claim 5, wherein step 1) comprises 3 applications of the aqueous or aqueous-alcoholic solution to the skin area of the individual.

7. The method of claims 1, wherein the skin area is the bend of the arm, the lobe of the ear, the posterior face of the pinna of the ear, the face, the wing of the nose, the nasogenial sulcus or the point of the lower maxillary.

8. The method of claim 1, wherein the aqueous-ethanolic solution comprises 10% ethanol in water.

9. The method of claim 1, wherein the capsaicinoid is a natural capsaicinoid, a synthetic capsaicinoid, a synthetic extract or a plant extract.

10. The method of claim 1, wherein in step 3) the concentration of stimulant increases by a factor of between 1.5 and 10.

11. The method of claim 10, wherein the concentration of stimulant increases by a factor of between 2 and 5.

12. The method of claim 10, wherein the concentration increases by a factor of the square root of 10.

13. The method of claim 1, wherein the concentration of stimulant in the first composition applied in step 1) is between $1 \times 10^{-5}\%$ and $6 \times 10^{-5}\%$.

14. The method of claim 13, wherein the concentration of stimulant in the first composition applied in step 1) is $3.16 \times 10^{-5}\%$.

15. The method of claim 1, wherein the skin area is the bend of the arm, the lobe of the ear, the posterior face of the pinna of the ear, the face, the wing of the nose, the nasogenial sulcus or the point of the lower maxillary.

16. The method of claim 15, wherein the skin area is the wing of the nose.

17. The method of claim 1, wherein the aqueous-ethanolic solution contains 10% of ethanol in water.

18. The method of claim 1, wherein step 1) is preceded by prior application to a skin area of a composition comprising the vehicle without stimulant.

19. The method of claim 1, wherein the concentration of stimulant in step 1) is between $3.16 \times 10^{-5}\%$ and $1 \times 10^{-3}\%$.

20. The method of claim 1, wherein the unattractive sensation is at least one selected from the group consisting of stinging, pins and needles, itching, pruritus, hotness and pulling.

21. A non-therapeutic method of evaluating the level of skin neurosensitivity of an adult individual to a capsaicinoid, the method comprising: a) applying a composition comprising a physiologically acceptable vehicle that is an aqueous or aqueous-alcoholic solution to a skin area of a subject; b) recording whether the subject perceived an unattractive sensation on the skin area having received the vehicle; c) if so, stopping the test; if not, applying to a skin area, optionally to the same area having received the vehicle previously, the same vehicle containing a peripheral nervous system stimulant that is a capsaicinoid at a concentration of between $1\times10^{-5}$% and $1\times10^{-3}$%; d) recording whether the subject perceived an unattractive sensation on the skin area having received the composition containing the stimulant; e) if so, recording the concentration of stimulant and stopping the test; if not, increasing the concentration of stimulant by a factor of between 1.5 and 10, and repeating steps c) to e) n times, where n is between 1 and 10, wherein the aqueous-ethanolic solution contains from 8% to 15% ethanol in water, wherein the unattractive sensation perceived is scored on a scale of 0 to 5, wherein 0 represents no sensation, 1 represents very slight sensation, 2 represents slight sensation, 3 represents moderate sensation, 4 represents substantial sensation, and 5 represents painful sensation, and wherein an individual is declared to have sensitive skin if the score is greater than or equal to 5 after 5 minutes or if a moderate sensation is perceived during the first three minutes.

22. The method of claim 21, further comprising waiting for 120 to 360 seconds at least one of after step a) and before step b) and after step c) and before step d).

23. The method of claim 22, wherein the waiting is for 120 to 200 seconds.

24. The method of claim 22, wherein the waiting is for 180 seconds.

25. The method of claim 21, wherein step a) is preceded by prior application to a skin area and to its area on the opposite side of a composition comprising the vehicle without stimulant.

26. The method of claim 21, wherein the concentration of stimulant in step c) is between $3.16\times10^{-5}$% and $1\times10^{-3}$%.

27. The method of claim 21, wherein the aqueous-ethanolic solution contains 10% of ethanol in water.

28. The method of claim 21, wherein the unattractive sensation is at least one selected from the group consisting of stinging, pins and needles, itching, pruritus, hotness and pulling.

29. A non-therapeutic method of evaluating the level of skin neurosensitivity of an adult individual to a capsaicinoid, the method comprising a) applying a composition comprising a physiologically acceptable vehicle that is an aqueous or aqueous-alcoholic solution to a skin area and to its area on the opposite side; b) recording whether the subject perceived an unattractive sensation on at least one of the areas having received the vehicle; c) if so, stopping the test; if not, applying to a skin area, the same vehicle containing a peripheral nervous system stimulant that is a capsaicinoid at concentration of between $1\times10^{-5}$% and $1\times10^{-3}$%; and applying the same vehicle to the area on the opposite side; d) recording whether the subject perceived a discriminating unattractive sensation on the skin area having received the vehicle containing the stimulant in relation to the skin area on the opposite side; and e) if so, recording the concentration of stimulant and stopping the test; if not, increasing the concentration of stimulant by a factor of between 1.5 and 10, and repeating steps c) to e) n times, where n is between 1 and 10, wherein the aqueous-ethanolic solution contains from 8% to 15% ethanol in water, wherein the unattractive sensation perceived is scored on a scale of 0 to 5, wherein 0 represents no sensation, 1 represents very slight sensation, 2 represents slight sensation, 3 represents moderate sensation, 4 represents substantial sensation, and 5 represents painful sensation, and wherein an individual is declared to have sensitive skin if the score is greater than or equal to 5 after 5 minutes or if a moderate sensation is perceived during the first three minutes.

30. The method of claim 29, further comprising waiting for 120 to 360 seconds at least one of after step a) and before step b) and after step c) and before step d).

31. The method of claim 30, wherein the waiting is for 120 to 200 seconds.

32. The method of claim 30, wherein the waiting is for 180 seconds.

33. The method of claim 29, wherein the concentration of stimulant in step c) is between $3.16\times10^{-5}$% and $1\times10^{-3}$%.

34. The method of claim 29, wherein the aqueous-ethanolic solution contains 10% of ethanol in water.

35. The method of claim 29, wherein the unattractive sensation is at least one selected from the group consisting of stinging, pins and needles, itching, pruritus, hotness and pulling.

\* \* \* \* \*